(12) United States Patent
Tsao et al.

(10) Patent No.: US 7,550,418 B2
(45) Date of Patent: Jun. 23, 2009

(54) LENS CARE COMPOSITION AND METHOD

(75) Inventors: Fu-Pao Tsao, Lawrenceville, GA (US); Karen Frances Lindley, Cumming, GA (US)

(73) Assignee: Novartis AG, Basel (CH)

( * ) Notice: Subject to any disclaimer, the term of this patent is extended or adjusted under 35 U.S.C. 154(b) by 264 days.

(21) Appl. No.: 10/722,008

(22) Filed: Nov. 25, 2003

(65) Prior Publication Data
US 2004/0142829 A1    Jul. 22, 2004

Related U.S. Application Data

(60) Provisional application No. 60/433,173, filed on Dec. 13, 2002.

(51) Int. Cl.
*C11D 43/00* (2006.01)

(52) U.S. Cl. ......... 510/112; 510/115; 514/840

(58) Field of Classification Search ......... None
See application file for complete search history.

(56) References Cited

U.S. PATENT DOCUMENTS

| | | | |
|---|---|---|---|
| 4,758,595 A | 7/1988 | Ogunbiyi et al. | 514/635 |
| 4,836,986 A | 6/1989 | Ogunbiyi et al. | 422/28 |
| 5,756,045 A | 5/1998 | Mowrey-McKee et al. | 422/28 |
| 6,037,328 A * | 3/2000 | Hu et al. | 514/23 |
| 6,121,327 A | 9/2000 | Tsuzuki et al. | 514/642 |
| 6,143,244 A | 11/2000 | Xia et al. | 422/28 |
| 6,172,017 B1 | 1/2001 | Groemminger et al. | 510/112 |
| 6,369,112 B1 | 4/2002 | Xia | 514/635 |
| 6,482,781 B2 | 11/2002 | Graham et al. | 510/112 |
| 6,486,215 B2 | 11/2002 | Asgharian | 514/839 |
| 6,872,695 B1 * | 3/2005 | Groemminger et al. | 510/112 |
| 2002/0114729 A1 | 8/2002 | Salamone et al. | 422/28 |
| 2002/0115578 A1 | 8/2002 | Groemminger | 510/112 |
| 2002/0155961 A1 * | 10/2002 | Schwind et al. | 510/112 |
| 2006/0148665 A1 * | 7/2006 | Smith | 510/126 |

FOREIGN PATENT DOCUMENTS

| | | |
|---|---|---|
| JP | 10-108899 | 4/1998 |
| WO | WO 02/38161 | 5/2002 |

OTHER PUBLICATIONS

Standard Search Report, Dec. 7, 2003.

* cited by examiner

*Primary Examiner*—Necholus Ogden, Jr.
(74) *Attorney, Agent, or Firm*—Sheng-Hsin Hu; Robert Gorman

(57) ABSTRACT

An buffered aqueous contact lens disinfecting solution having much lower concentration of disinfecting agents, and less irritating to the eye. The solutions have a tonicity of 200 to 450 mOsm/kg, a pH of between 6 and 8, and a concentration of chloride ions below 1500 ppm. Despite having less than 1 ppm of antimicrobial, the solutions are effective against *C. albicans* within 15 minutes of contact.

5 Claims, No Drawings

LENS CARE COMPOSITION AND METHOD

This application claims under 35 USC § 119 (e) the benefit of the filing date of U.S. Provisional Application No. 60/433,173 filed Dec. 13, 2002 and all references incorporated therein.

FIELD OF THE INVENTION

The present invention relates to compositions for treating, for example, disinfecting, cleaning, soaking, conditioning and wetting contact lenses. More particularly, the invention relates to multi-purpose solutions useful in treating contact lenses, for example, for disinfecting contact lenses, for removing deposit material from contact lenses, for soaking, conditioning and/or wetting contact lenses and the like, which provide substantial comfort and acceptability benefits to the users of such solutions.

DESCRIPTION OF RELATED ART

Contact lenses need to be periodically treated, for example, disinfected, cleaned, soaked and the like, on a regular basis because of the tendency for a variety of ocular and environmental contaminants, microbes and other materials to accumulate on the lenses and/or the need to provide the lenses in suitable condition for safe and comfortable wear. User compliance, that is users treating contact lenses on a regular and consistent basis, is important in order to promote ocular health and to avoid problems associated with contact lens wear. User compliance is enhanced when the treatment solution employed provides high degrees of lens wearer/user comfort and acceptability. Therefore, it would be advantageous to provide compositions for treating contact lenses which provide such comfort and/or are accepted by contact lens wearers/users of such compositions.

British Pat. No. 1,432,345 disclosed contact lens disinfecting compositions containing a polymeric biguanide and a phosphate buffer. The concentration of the disinfecting polymer disclosed by this patent is substantially higher than that of the present invention.

Higher concentrations of biguanides are detrimental to wearer comfort because they tend to bind to and concentrate within soft contact lenses. While low levels of such compounds may not lead to ocular irritation when used properly, they can reach potentially dangerous levels if concentrated within a contact lens and may cause corneal inflammation and other eye tissue irritation. Furthermore, recent investigations have indicated that polymeric biguanides may play a role in dry eye symptoms of contact lens wearers.

U.S. Pat. No. 4,758,595 to Ogunbiyi, et al., discloses contact lens disinfecting compositions containing a biguanide and a borate buffer. While the concentration of biguanide in the disclosed solutions is lower than previously taught, because large concentrations of chloride ion are present, the solutions are not particularly effective against *Candida albicans* at such low levels of biguanide.

PCT publication WO 02/38161 to Smith discloses polyhexamethylene biguanide ("PHMB") disinfecting solutions containing less than 0.2%, by weight, sodium chloride. However, because the solutions still add considerable amounts of sodium chloride for tonicity and use hydrochloric acid for pH adjustment, the solutions still contain significant amounts of chloride ion. As a result, in order to maintain disinfecting properties, the solutions must have a minimum of 1 ppm PHMB.

Accordingly, there is a need for improved disinfecting and preservative solutions which are compatible for use with soft contact lenses, while maintaining both a high level of antibacterial activity, particularly against *C. albicans*. Furthermore, there is a need for improved preservative systems that maintain a low order of toxicity and irritation to tissue in and surrounding the eye.

SUMMARY OF THE INVENTION

It has been surprisingly discovered that a solution having an antimicrobial concentration significantly lower than previously disclosed can be effective against *C. albicans*, if the solution is substantially free of compounds having a negative or partially negative charged moiety, such as halides, alkaline earth halides, compounds with a carboxylic functional group, compounds with a sulfate functional group, compounds with a phosphate functional group, and compounds of phenolics. Particularly effective are those solutions wherein the concentration of such groups as ions is below 1500 ppm.

In one aspect, the present invention provides a buffered aqueous solution for disinfecting and/or preserving items such as contact lenses comprising less than or equal to 1 ppm of an antimicrobial compound or water soluble salts thereof, having a tonicity in the range 200 to 450 mOsm/kg, a pH in the range of 6 to 8, and being substantially free of chloride ions. By substantially free of chloride ions, it is meant that the concentration of such ions is below 1500 ppm.

In another aspect, the present invention provides a buffered aqueous solution for disinfecting and/or preserving items such as contact lenses comprising microbiocidally effective amounts of a biguanide or water soluble salts thereof, having a tonicity in the range 200 to 450 mOsm/kg, a pH in the range of 6 to 8, and being substantially free of negatively charged ions having an affinity for PHMB, such as chloride and phosphate ions. By substantially free of chloride and phosphate ions, it is meant that the total concentration of such ions is below 1500 ppm.

In a further aspect, the present invention provides a buffered aqueous solution for disinfecting and/or preserving items such as contact lenses comprising less than or equal to 1 ppm of a biguanide or water soluble salts thereof, having a tonicity in the range 200 to 450 mOsm/kg, wherein the majority of the tonicity of the solution is provided by one or more compounds selected from the group consisting of non-halide containing electrolytes and non-electrolytic compounds. By non-electrolyte, it is meant those compounds that do not dissociate into ions in water.

In yet another aspect, the invention provides a buffered aqueous solution for disinfecting and/or preserving items such as contact lenses comprising less than or equal to 1 ppm of a biguanide or water soluble salts thereof and less than 1000 ppm chloride ion. The buffer has a pKa of greater than 8.0 and either has a positive charge or no charge at a neutral pH (e.g., TRIS, bis-TRIS-propane).

In yet another aspect, the invention provides a phosphate buffered aqueous solution for disinfecting and/or preserving items such as contact lenses comprising less than or equal to 1 ppm of a biguanide or water soluble salts thereof; less than 1000 ppm chloride ion; and phosphate buffer at a concentration less than 0.1%.

The invention also involves a method for disinfecting soft contact lenses comprising contacting a contact lens with a liquid medium containing less than 1 ppm of an antimicrobial, preferably a biguanide or water soluble salts thereof, having a tonicity in the range 200 to 450 mOsm/kg, a pH in the range of 6 to 8, and being substantially free of chloride and phosphate ions to thereby disinfect the contact lens These and other aspects and advantages of the present invention will become apparent in the detailed description, examples, and claims.

DETAILED DESCRIPTION OF THE PREFERRED EMBODIMENT

The present invention is directed to a composition, in the form of an aqueous solution comprising less than 1 ppm of a biguanide or water soluble salts thereof; and a method of using the solution for disinfecting and/or preserving contact lenses, especially soft contact lenses. The disinfecting solutions of the present invention are effective against a wide spectrum of microorganisms, including but not limited to *Staphylococcus aureus* (ATCC 6538), *Pseudomonas aeruginosa* (ATCC 9027), *Serratia marcescens* (ATCC 13880), *Candida albicans* (ATCC 10231), and *Fusarium solani* (ATCC 36031). Because *C. albicans* is typically the most difficult organism to kill, it is usually a good indicator of the overall effectiveness of a particular solution.

A disinfecting solution is generally defined as a contact lens care product containing one or more active ingredients (for example, antimicrobial agents and/or preservatives) in sufficient concentrations to destroy harmful microorganisms on the surface of a contact lens within the recommended minimum soaking time. The recommended minimum soaking time is included in the package instructions for use of the disinfecting solution. The present solution, in combination with its container or bottle and packaging, including instructions for use, may be considered a novel and improved kit, package, or system for the care of contact lenses.

The term "soft lens" means a lens having a proportion of hydrophilic repeat units such that the water content of the lens during use is at least 20% by weight. The term "soft contact lens" as used herein generally refers to those contact lenses which readily flex under small amounts of force. Typically, soft contact lenses are formulated from polymers having a certain proportion of repeat units derived from hydroxyethyl methacrylate and/or other hydrophilic monomers, typically crosslinked with a crosslinking agent. In contrast, conventional "hard contact lenses," which cover only a part of the cornea of the eye, usually consist of poly(methyl methacrylate) crosslinked with ethylene glycol dimethacrylate or the like, and conventional rigid gas permeable lenses (RGP) typically consists of monomers containing silicon that result in a more oxygen-permeable material. The solutions of the present invention, while adequate for cleaning hard contact lenses, are especially useful for cleaning and disinfecting soft contact lenses.

By the term "ophthalmically safe" with respect to a contact lens solution is meant that a contact lens treated with the solution is safe for direct placement on the eye without rinsing. That is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations. It is preferred that the solutions of the present invention be ophthalmically safe.

The term "compatible with the eye" means a solution that may be in intimate contact with the eye for an extended period of time without significantly damaging the eye and without significant user discomfort. It is preferred that the solutions of the present invention be compatible with the eye.

The term "disinfecting solution" means a solution containing one or more microbiocidal compounds, that is effective for reducing or substantially eliminating the presence of an array of microorganisms present on a contact lens, which can be tested by challenging a solution or a contact lens after immersion in the solution with specified inoculums of such microorganisms. The term "disinfecting solution" as used herein does not exclude the possibility that the solution may also be useful for a preserving solution or that the disinfecting solution may additionally be useful for daily cleaning, rinsing, and storage of contact lenses.

The term "cleaning" means that the solution contains one or more active ingredients in sufficient concentrations to loosen and remove loosely held lens deposits and other contaminants on the surface of the article to be cleaned. While not necessary with the present invention, a user may wish to use the solutions of the present invention in conjunction with digital manipulation (for example, manual rubbing of the lens with a solution) or with an accessory device that agitates the solution in contact with the lens, for example, a mechanical cleaning aid.

A solution that is useful for cleaning, chemical disinfection, storing, and rinsing an article, such as a contact lens, is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis.

The disinfecting compositions of the present invention will contain an antimicrobial agent. Antimicrobial agents may be either monomeric or polymeric antimicrobial agents that derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polyquaternium-1, which is a polymeric quaternary ammonium compound; and polyhexamethylene biguanide ("PHMB"), which is a polymeric biguanide. These preferred antimicrobial agents are disclosed in U.S. Pat. Nos. 4,407,791 and 4,525,346, to Stark, and U.S. Pat. Nos. 4,758,595 and 4,836,986, to Ogunbiyi, respectively. The entire contents of the foregoing publications are hereby incorporated in the present specification by reference. Other antimicrobial agents suitable in the compositions and methods of the present invention include other quaternary ammonium compounds, such as benzalkonium halides, and other biguanides, such as chlorhexidine. The preferred antimicrobial agent is a biguanide, most preferably a polymeric biguanide.

The solutions of the invention contain an antimicrobial agent, preferably a biguanide, in a concentration that is suitable for disinfecting purposes, preferably about less than 1 ppm, more preferably from about 0.01 ppm to 0.9 ppm; most preferably less than 0.5 ppm, especially about 0.25 ppm.

The presently useful antimicrobial biguanides include biguanides, biguanide polymers, salts thereof, and mixtures thereof. Preferably, the biguanide is selected from alexidine free-base, salts of alexidine, chlorhexidine free-base, salts of chlorhexidine, hexamethylene biguanides, and their polymers, and salts thereof. Most preferably, the biguanide is a hexamethylene biguanide polymer (PHMB), also referred to as polyaminopropyl biguanide (PAPB).

It has been surprisingly discovered that the comparatively low levels of biguanides contemplated in this invention are effective against a broad spectrum of microorganisms, including C. albicans, in a solution having less than 1500 ppm of chloride ion. Preferably, the solution contains a concentration of chloride ions less than 1000 ppm; more preferably less than 500 ppm; and most preferably lower than 250 ppm.

Preferably, the solutions of the present invention have a low concentration of phosphate ions, preferably substantially free of phosphate ions. Solutions having less than a total of 1500 ppm of phosphate ion and chloride ion have been surprisingly discovered to be effective against a broad spectrum of microorganisms, including C. albicans. Preferably, the solution contains a concentration of chloride ions less than 1000 ppm; more preferably less than 500 ppm; and most preferably lower than 250 ppm. Previously known solutions generally had very high concentrations of both phosphate ions and chloride ions, due to their use large amounts of phosphate buffers, sodium or potassium chloride tonicity agents, and hydrochloric or phosphoric acid to adjust pH downward. While such buffers, tonicity agents, and pH adjusters may be used in the present invention, they must be used in amounts less than would result in ion concentrations higher than defined by the invention.

The composition of the present invention preferably contains a buffer. The buffer maintains the pH preferably in the desired range, for example, in a physiologically acceptable range of about 6 to about 8.5; or about 6 to about 7; or about 7 to about 8. In particular, the solution preferably has a pH in the range of about 6.5 to about 7.5, most preferably from about 6.8 to about 7.6.

Suitable buffer substances as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (trometamol, 2-amino-2-hydroxymethyl-1,3-propanediol), bis-TRIS-propane, phosphate buffers, e.g. $Na_2HPO_4$, $NaH_2PO_4$, and $KH_2PO_4$ or mixtures thereof. However, if phosphate buffers are used, they should be used at total concentrations less than 0.1%, preferably less than 0.06%, more preferably less than 0.05%, most preferably about 0.02%. It has been found that even concentrations less than 0.015% of phosphate buffer will provide a useful solution.

Alternatively, if a buffer such as TRIS is added to the solution at typical concentrations, the pH will be greater than 9.0 and must be adjusted downwardly. In the past it has been typical to employ hydrochloric acid to lower the pH. Because such an addition added additional chloride ions to the solution, it is preferred to either lower the concentration of TRIS to minimize the amount of acid needed to reach a suitable pH, and/or to use acids not containing chloride or phosphate ions. Of course, it is within the scope of this invention to utilize hydrochloric and/or phosphoric acid to adjust pH downwardly, so long as the concentration of chloride and phosphate ions in the solution does not exceed that range defining the present invention. Additionally, TRIS buffer is often supplied as TRIS•HCl, which introduces additional chloride ion into the solution. Accordingly, it is preferred when using a buffer, such as TRIS, to use what is known as the "free-base" form that does not include HCl.

The contact lens care solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308mOsm/kg). Sodium chloride or potassium chloride has been used as the tonicity agent in the majority of contact lens solutions in the art. However, a 0.9% sodium chloride solution would result in almost 5500 ppm chloride ion in the solution. Such a high concentration of chloride ion would diminish the effectiveness of PHMB, and would not be within the scope of this invention. Accordingly, the solutions of the present invention, especially those having less than 0.5 ppm PHMB, preferably use no more than about 0.25% sodium chloride and no more than about 0.36% potassium chloride. More preferably, both sodium chloride and potassium chloride, if present at all, are present at less than 0.1%, most preferably less than 0.05%. Especially preferred are those solutions having no sodium chloride or potassium chloride.

Accordingly, the isotonicity with the lachrymal fluid, or even another desired tonicity, may be adjusted by adding organic or inorganic substances that affect the tonicity. The former may be used e.g. in amounts of about 1 to 20 percent by weight, and the latter in amounts of about 0.1 to 5 percent by weight. In general the amount to be added of the substance which affects tonicity, is such that the tonicity of the composition according to the invention is in particular in the range 200 to 450 mOsm/kg, preferably in the range 220 to 330 mOsm/kg, most preferably in the range of 220 to 310 mOsm/kg. Typical organic substances of this kind are, for example, glycerol, urea, propylene glycol, polyols, or carbohydrates and sugars such as mannitol or sorbitol, and typical inorganic substances of this kind include alkali or alkali earth metal halides, sulfates, nitrates, carbonates, and borates. Mixtures of these compounds with one another may also be used according to the invention. As stated above, it is not preferable to use either potassium chloride or sodium chloride. Instead, it is preferred to use a non-chloride containing tonicity agent, preferably mannitol or sorbitol, with sorbitol being the most preferred. When non-contact lens cleaning is the desired use, the tonicity builder may also be absent or in even greater amounts than set forth above.

The addition of sorbitol to adjust the tonicity of contact lens care products is known. GB 2,205,175 and U.S. Pat. No. 3,888,782 describe sorbitol as a carrier material for the preparation of powder mixtures for contact lens care products. It has been found that sorbitol may aid in stabilizing the lachrymal film after inserting the contact lenses, whereupon a heavy loss of the aqueous layer is prevented. This guards against the appearance of dryness, which can lead to a reduced lachrymal film. Negative effects caused by surface-active substances and preservatives are reduced and the contact lenses are prevented from drying out.

Furthermore, sorbitol is not cytotoxic and does not have negative effects on the antimicrobial efficacy of the solutions. It has surprisingly been found that the addition of sorbitol substantially increases the microbiological efficacy of antimicrobial compounds present in the contact lens care compositions according to the invention, e.g. of PHMB, without resulting in negative effects as regards toxicity.

Sorbitol is used in the preferred contact lens care compositions according to the invention in an amount of about 0.4 to about 18 percent by weight, especially in an amount of 2 to 8 percent by weight, more preferably in an amount of 3 to 6 percent by weight, most preferably in an amount of 4 to 6 percent by weight.

The solution may also contain one or more viscosity inducing agents. The viscosity inducing components preferably are effective at low or reduced concentrations, are compatible with the other components of the present solutions and are nonionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity inducing component may also act to cushion the impact on the eye surface during insertion and serves also to alleviate eye irritation.

Suitable viscosity inducing components include, but are not limited to, polyvinylpyrrolidone, water soluble natural gums, cellulose-derived polymers, and the like. Useful natural gums include guar gum, gum tragacanth and the like. Useful cellulose-derived viscosity inducing components include cellulose-derived polymers, such as hydroxypropyl cellulose, hydroxypropylmethyl cellulose, carboxymethyl cellulose, methyl cellulose, hydroxyethyl cellulose and the like. More preferably, the viscosity inducing agent is selected from cellulose derivatives (polymers) and mixtures thereof. A very useful viscosity inducing component is polyvinylpyrrolidone (PVP).

The polyvinylpyrrolidone (PVP) used in the compositions of the invention is a linear homopolymer or essentially a linear homopolymer comprising at least 90% repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrolidinone, and 1-ethenyl-2-pyrolionone (CAS registry number 9003-39-8). The PVP used in the present invention suitably has a weight average molecular weight of about 10,000 to 250,000, preferably 30,000 to 100,000. Such materials are sold by various companies, including ISP Technologies, Inc. under the trademark PLASDONE™ K-29/32, from BASF under the trademark KOLLIDON™ for USP grade PVP, for example KOLLIDON™ K-30 or K-90. While the invention is not limited to any specific PVP, K-90 PVP is preferred, more preferably pharmaceutical grade.

A multi-purpose solution preferably has a viscosity of less than 75 cps, preferably 1 to 50 cps, and most preferably 1 to 25 cps. The viscosity inducing component is used in an amount effective to increase the viscosity of the solution, preferably to a viscosity in the range of about 1.0 to about 30, or even as high as about 1000, cps at 25° C., preferably less than 75 cps, most preferably less than 25, as determined by USP test method No. 911. To achieve this range of viscosity increase, an amount of viscosity inducing component of about 0.01% to about 5% (w/v) preferably is employed, with amounts of about 0.05% to about 0.5% being more preferred. The viscosity of the solution preferably is not above 1000 cps, preferably not above 750 cps, most preferably not above 25 cps at any pH between 6.0 and 8.0, preferably between 6.5 and 7.5, as such changes in viscosity may be detrimental to the performance of a soft contact lens.

The solutions of the present invention may optionally include a surface active agent for cleaning the contact lens. A wide variety of surface active agents are known in the art, including anionic, cationic, nonionic and amphoteric surface active agents. As it is believed that certain ionic surface active agents are detrimental to the antimicrobial action of PHMB, non-ionic surface active agents are especially preferred.

Nonionic surface active agents having good cleaning activity include certain polyoxyethylene, polyoxypropylene block copolymer (poloxamer) surface active agents, including various surface active agents available under the tradename Pluronic from BASF Corp., e.g., PLURONIC P104 or L64. Other representative nonionic surface active agents include: ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); and alkyl glucosides and polyglucosides such as products available under the tradename PLANTAREN (Henkel Corp., Hoboken, N.J., USA). The preferred surface active agents include polyethoxylated castor oils. These surfactants are commercially available from BASF under the trademark CREMAPHOR.

The surface active agents having cleaning activity for contact lens deposits may be employed at about 0.001 to about 5 weight percent of the composition, preferably at about 0.005 to about 2 weight percent, with about 0.01 to about 0.5 weight percent being especially preferred.

Preferred surface active agents include homopolymers of polyethylene glycol or polyethyleneoxide, and certain poloxamers such as materials commercially available from BASF under the tradenames PLURONIC 17R4, PLURONIC F-68NF, PLURONIC F68LF, and PLURONIC F127, with PLURONIC F-68NF (National Formulary grade) being the most preferred. When present, poloxamers may be employed at about 0.001 to about 10 weight percent, preferably at about 0.01 to about 1 weight percent, more preferably from 0.05% to 0.2%.

The solutions of the present invention preferably contain dexpanthenol, an alcohol of pantothenic acid. Dexpanthenol may be used in the solutions according to the invention in an amount of 0.005% to 10%, especially in an amount of 0.01 to 5%, preferably in an amount of 0.01 to 1%, more preferably in an amount of 0.01 to 0.5%, most preferably from about 0.01 to 0.1%.

The solutions of the present invention preferably contain tyloxapol. Tyloxapol is an oxyethylated tertiary octylphenol formaldehyde polymer, commercially available from Rohm & Haas Co. (Philadelphia, Pa.). Tyloxapol is a nonionic surfactant with surface tension reducing properties that is freely soluble in water. The tyloxapol is suitably employed in concentrations ranging from 0.005 to 1.0%, preferably 0.01 to 0.5%, most preferably about 0.01% to 0.03%. If the solution contains tyloxapol, it also preferably contains a poloxamer or a mixture of poloxamers in a concentration from 0.05% to 1%, preferably from 0.05% to 0.5%, more preferably about 0.05% to 0.2%.

The present compositions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. Preferably, the present solutions include chelating components in effective amounts less than about 0.02% (w/v); especially 0.01% (w/v) or less; more preferably less than 0.008%, and most preferably between 0.003% and 0.005%. Such reduced amounts of chelating component in the present compositions remain effective in providing the desired chelating and/or sequestering functions while, at the same time, are better tolerated in the eye, thereby reducing the risk of user discomfort and/or ocular irritation. Furthermore, it has been surprisingly discovered that EDTA has an inhibitory effect on the antimicrobial properties of PHMB at concentrations normally used in lens care solutions. The concentrations described herein do not adversely affect the antimicrobial properties to a significant degree.

In another embodiment of the present invention the majority of the tonicity of the solution is provided by one or more compounds selected from the group consisting of non-halide containing electrolytes (e.g., sodium bicarbonate) and non-electrolytic compounds. By non-electrolyte, it is meant those compounds that do not readily dissociate into ions in water. Examples include, but are not limited to, sorbitol, mannitol, glycerol, propylene glycol, xylitol, and inositol. Such solutions have a tonicity in the range 200 to 450 mOsm/kg, preferably in the range 220 to 330 mOsm/kg, most preferably in the range of 270 to 310 mOsm/kg, and at least 50% of the tonicity of the solution will be provided by one or more non-halide containing electrolytes or non-electrolytic compounds. Specifically, at least 65%, preferably at least 75%, more preferably at least 85%, and most preferably at least 95% of the tonicity of the solution will be provided by one or more non-halide containing electrolytes or non-electrolytic compounds.

Even more preferred are solutions wherein non-electrolytic compounds provide at least 50% of the tonicity of the solution. More specifically, at least 65%, preferably at least 75%, more preferably at least 85%, and most preferably at least 95% of the tonicity of the solution will be provided by one or more non-electrolytic compounds. Specifically preferred are solutions having at least 3% sorbitol, more preferably at least 4% sorbitol, and most preferably at least 5% sorbitol.

In solutions where at least 50% of the tonicity of the solution is provided by non-electrolytic compounds, the concentration of the biguanide anti-microbial compound can be greatly reduced. For example, the preferred anti-microbial compound, PHMB, can be employed effectively in a disinfecting solution against *C. albicans* at a concentration as low as 1 ppm, or even as low as 0.1 ppm. More preferably, PHMB is present less than or equal to 0.5 ppm, especially less than 0.5 ppm, more preferably less than or equal to 0.25 ppm, and most preferably less than or equal to 0.15 ppm.

While it is generally preferred for the solutions of the present invention to be virtually free of chloride ions, yet another embodiment of the present invention are solutions having low amounts of phosphate ions from small concentrations of phosphate buffer. It has been surprisingly found that solutions having less than 1000 ppm chloride ion and containing phosphate buffer at a concentration less than 0.1% will provide better cleaning abilities, while maintaining antimicrobial efficacy, as compared to solutions without phosphate buffers. Preferably, solutions containing phosphate buffer will have less than 500 ppm chloride ion, more preferably less than 250 ppm chloride ion, and most preferably less than 100 ppm chloride ion. Furthermore, it is preferred that the total concentration of phosphate buffers ($Na_2HPO_4$, $NaH_2PO_4$, and $KH_2PO_4$, and mixtures thereof) is less than 0.06%, more preferably less than 0.025%, and most preferably between about 0.005% and 0.015%.

Because the various phosphate buffers contribute differing amounts of phosphate ion to solution from the same percent by weight of buffer, the invention can alternatively be described in terms of ppm phosphate ion in the solution. In this manner, it is preferred that a phosphate buffered solution contain less than 800 ppm phosphate ion; especially less than 500 ppm phosphate ion, more preferably less than 200 ppm phosphate ion; most preferably between 40 ppm and 120 ppm phosphate ion. If less than about 0.25 ppm PHMB is present in the solution, it may be desirable to reduce the phosphate concentration even further.

Aqueous solutions comprising the following components have been found to be particularly useful in disinfecting contact lenses:

| | |
|---|---|
| PHMB | less than 1 ppm |
| dexpanthenol | 0.005% to 1% |
| tyloxapol | 0.01% to 1% |
| $Na_2HPO_4$ | less than 0.06% |
| EDTA | less than 0.2% |
| poloxamer | 0.01% to 1% |
| PVP | 0.01% to 1% |
| Sorbitol | at least 1% |
| Chloride ion | less than 1000 ppm |

Even more preferred are those solutions having the following components:

| | |
|---|---|
| PHMB | less than 0.5 ppm |
| dexpanthenol | 0.01% to 0.1% |
| tyloxapol | 0% to 0.5% |
| $Na_2HPO_4$ | 0.001% to 0.05% |
| EDTA | 0.003% to 0.005% |
| poloxamer | 0.001% to 0.5% |
| PVP | 0.1% to 0.3% |
| Sorbitol | at least 4% |
| Chloride ion | less than 500 ppm |

Methods for treating a soft contact lens using the compositions described herein are included within the scope of the invention. Such methods comprise contacting a soft contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 37° C. Contacting at or about ambient temperature is very convenient and useful. The contacting preferably occurs at or about atmospheric pressure. The contacting preferably occurs for a time in the range of about 5 minutes or about 1 hour to about 12 hours or more. Especially preferred are those solutions have less than 0.5 ppm PHMB and can obtain at least a 1 log reduction in *C. albicans* within 15 minutes of contact with the lens. Also preferred are those having less than 0.25 ppm PHMB and obtaining at least 1.0, more preferably 1.5 log, reduction in *C. albicans* within 15 minutes, more preferably at least a 2.0 log reduction in *C. albicans* within 30 minutes.

The contact lens can be contacted with the solution by immersing the lens in the solution. Although not necessary, the solution containing the contact lens can be agitated, for example, by shaking the container containing the solution and contact lens, to at least facilitate removal of deposit material from the lens.

The solutions and methods of the present invention may be used in conjunction with enzymes to remove debris or deposit material from the contact lens as the solutions of the present invention have no negative effect on the proteolytic activity of enzymes, such as UNIZYME®. After such contacting step, the contact lens optionally may be manually rubbed with saline, or even rinsed without rubbing, to remove further deposit material from the lens. The cleaning method can also include rinsing the lens substantially free of the liquid aqueous medium prior to returning the lens to a wearer's eye.

The following non-limiting examples illustrate certain aspects of the present invention.

EXAMPLES

Example 1

A solution according to the present invention was prepared by blending the following components:

| | |
|---|---|
| PHMB | 0.5 ppm |
| bis-TRIS-propane | 0.1% |
| dexpanthenol | 0.02% |
| sorbitol | 4% |
| PLURONIC F-127 | 0.1% |
| tyloxapol | 0.02% |
| phosphoric acid | pH to 6.860 |

The tonicity of the solution was 237 mOsm/kg.

Example 2

A solution according to the present invention was prepared by blending the following components:

| | |
|---|---|
| PHMB | 0.25 ppm |
| bis-TRIS-propane | 0.1% |
| dexpanthenol | 0.02% |
| sorbitol | 5% |
| PLURONIC F-127 | 0.1% |
| tyloxapol | 0.02% |
| phosphoric acid | pH to 7.040 |

The tonicity of the solution was 280 mOsm/kg.

Example 3

A solution according to the present invention was prepared by blending the following components:

| | |
|---|---|
| PHMB | 0.25 ppm |
| tromethamine | 0.1% |
| dexpanthenol | 0.02% |
| sorbitol | 5% |
| PLURONIC F-127 | 0.1% |
| tyloxapol | 0.02% |
| boric acid | pH to 7.203 |

The tonicity of the solution was 281 mOsm/kg.

Example 4

A solution according to the present invention was prepared by blending the following components:

| | |
|---|---|
| PHMB | 0.25 ppm |
| tromethamine | 0.1% |
| dexpanthenol | 0.02% |
| sorbitol | 5% |
| PLURONIC F-127 | 0.1% |
| tyloxapol | 0.02% |
| phosphoric acid | pH to 7.394 |

The tonicity of the solution was 295 mOsm/kg.

Example 5

A solution according to the present invention was prepared by blending the following components:

| | |
|---|---|
| PHMB | 1.0 ppm |
| bis-TRIS-propane | 0.1% |
| dexpanthenol | 1.0% |
| sorbitol | 4% |
| PLURONIC F-127 | 0.1% |
| CHEMOPHORE RH40 | 0.1% |
| phosphoric acid | pH to 6.954 |

The tonicity of the solution was 287 mOsm/kg.

Example 6

A solution according to the present invention was prepared by blending the following components:

| | |
|---|---|
| PHMB | 1.0 ppm |
| bis-TRIS-propane | 0.1% |
| dexpanthenol | 0.2% |
| sorbitol | 4% |
| PLURONIC F-127 | 0.1% |
| tyloxapol | 0.02% |
| phosphoric acid | pH to 7.095 |

The tonicity of the solution was 241 mOsm/kg.

Example 7

A solution according to the present invention was prepared by blending the following components:

| | |
|---|---|
| PHMB | 1.0 ppm |
| bis-TRIS-propane | 0.1% |
| dexpanthenol | 0.1% |
| sorbitol | 4% |
| PLURONIC F-127 | 0.1% |
| CHEMOPHORE RH40 | 0.1% |
| phosphoric acid | pH to 7.060 |

The tonicity of the solution was 243 mOsm/kg.

Example 8

A series of tests were conducted to evaluate the disinfecting performance against *C. albicans* of solutions prepared in accordance with Examples 1-7 compared with two other solutions. The first of these solutions, referred hereinafter as Composition A, is a commercially available solution sold under the trademark RENU® MultiPlus containing 1.0 ppm of a polymeric biguanide and sodium chloride as the tonicity agent. The second, referred hereinafter as Composition B, is a commercially available solution sold under the trademark SOLOCARE® PLUS containing 1.0 ppm of a polymeric biguanide and sodium chloride as a tonicity agent.

TABLE 1

| Example | Polymeric Biguanid (ppm) | Log reduction (*C. albicans*) | |
|---|---|---|---|
| | | 15 min. | 30 min. |
| 1 | 0.5 | 3.9 | 4.6 |
| 2 | 0.25 | 1.6 | 2.7 |
| 3 | 0.25 | 1.5 | 2.0 |
| 4 | 0.25 | 1.7 | 2.2 |
| 5 | 1.0 | 3.2 | — |
| 6 | 1.0 | 4.0 | — |
| 7 | 1.0 | 3.7 | — |
| Composition A | 1.0 | 3.3 | 4.4 |
| Composition B | 1.0 | 0.4 | 0.7 |

These results show the effectiveness of phosphate- and NaCl-free solutions with antimicrobial concentrations as low as 0.25 ppm as compared to the phosphate- and NaCl-containing Composition B, with at least four times the antimicrobial component.

Examples 9-13

To demonstrate the effectiveness of low-chloride lens care solutions having PHMB concentrations of 0.25 ppm, several solutions according to the present invention were prepared by blending the following components:

| | |
|---|---|
| PHMB | 0.25 ppm |
| dexpanthenol | 0.02% |
| tyloxapol | 0.02% |
| Na$_2$HPO$_4$ | 0.01% |
| PLURONIC 17R4 | 0.05% |
| PVP (K-90) | 0.4% | and the following additional components as shown in Table 2. The solutions were tested against *C. albicans* with an inoculum level of 5.38 CFM/mL.

TABLE 2

| | Ex. 9 | Ex. 10 | Ex. 11 | Ex. 12 | Ex. 13 |
|---|---|---|---|---|---|
| Pluronic F-127 (%) | 0.1 | — | 0.1 | — | 0.1 |
| Propylene glycol (%) | 0.2 | 0.2 | — | — | — |
| Sorbitol (%) | 5 | 4 | 5 | 4 | 5 |
| PLURONIC F-68NF (%) | — | 0.1 | — | 0.1 | — |
| Isopropanol (%) | — | — | 0.2 | 0.2 | — |
| EDTA (%) | — | — | — | — | 0.004 |
| pH | 7.3-7.5 | 7.2-7.4 | 7.43 | 7.2-7.4 | 7.081 |
| log reduction (15 mins.) | 1.52 | 1.89 | 1.85 | 2.25 | 2.68 |

These results show the effectiveness of NaCl-free solutions (but with low levels of phosphate buffer) with antimicrobial concentrations as low as 0.25 ppm as compared to the NaCl-containing (but with higher levels of phosphate buffer) Composition B in Examples 8, with at least four times the antimicrobial component.

Examples 14-16

To demonstrate the effectiveness of additional low-chloride solutions with PHMB concentrations of 0.25 ppm, several solutions according to the present invention were prepared by blending the following components:

| | |
|---|---|
| PHMB | 0.25 ppm |
| dexpanthenol | 0.02% |
| tyloxapol | 0.02% |
| Na$_2$HPO$_4$ | 0.01% |
| PLURONIC F-68NF | 0.1% |
| Sorbitol | 5% | and the following additional components as shown in Table 3. The solutions were tested against *C. albicans* with an inoculum level of 5.38 CFM/mL.

TABLE 3

| | Ex. 14 | Ex. 15 | Ex. 16 |
|---|---|---|---|
| PVP(K-90) (%) | 0.4 | — | — |
| PLURONIC 17R4(%) | 0.05 | — | — |
| EDTA (%) | 0.004 | 0.004 | — |
| Sodium bicarbonate (%) | — | 0.007 | 0.007 |
| pH | 7.0-7.1 | 6.95 | 6.94 |
| log reduction (15 mins.) | 2.67 | 3.02 | 2.72 |

These results show the effectiveness of NaCl-free solutions (but with low levels of phosphate buffer) with antimicrobial concentrations as low as 0.25 ppm as compared to the NaCl-containing (but with higher levels of phosphate buffer) Composition B in Example 8, with at least four times the antimicrobial component.

Examples 17-20

To demonstrate the effectiveness of low-chloride solutions with EDTA, various grades of PVP, and PHMB concentrations of 0.25 ppm, several solutions according to the present invention were prepared by blending the following components:

| | |
|---|---|
| PHMB | 0.25 ppm |
| dexpanthenol | 0.02% |
| tyloxapol | 0.02% |
| Na$_2$HPO$_4$ | 0.01% |
| EDTA | 0.004% |
| Sorbitol | 5% | and the following additional components as shown in Table 4. The solutions were tested against *C. albicans* with an inoculum level of 5.7 CFM/mL.

TABLE 4

| | Ex. 17 | Ex. 18 | Ex. 19 | Ex. 20 |
|---|---|---|---|---|
| PLURONIC F-68LF | 0.1 | — | 0.1 | — |
| PLURONIC F-68NF | — | 0.1 | — | 0.1 |
| PLURONIC 17R4 (%) | 0.05 | 0.05 | — | — |
| PVP (K-90) (%) | 0.4 | 0.4 | — | 0.2 |
| PVP (K-25) (%) | — | — | 0.2 | — |
| Sodium bicarbonate (%) | — | 0.01 | 0.014 | 0.01 |
| pH | 6.962 | 6.939 | 6.913 | 6.978 |
| log reduction (15 mins.) | 2.78 | 3.14 | 3.03 | 3.28 |

Examples 21-22

To demonstrate the effectiveness of low-chloride solutions with EDTA, various grades of PVP, and PHMB concentrations of 0.125 ppm, several solutions according to the present invention were prepared by blending the following components:

| | |
|---|---|
| PHMB | 0.125 ppm |
| dexpanthenol | 0.02% |
| tyloxapol | 0.02% |
| Na$_2$HPO$_4$ | 0.01% |
| EDTA | 0.004% |
| Sorbitol | 5% | and the following additional components as shown in Table 5. The solutions were tested against *C. albicans* with an inoculum level of 5.7 CFM/mL.

TABLE 5

| | Ex. 21 | Ex. 22 |
|---|---|---|
| PLURONIC F-68LF | 0.1 | — |
| PLURONIC F-68NF | — | 0.1 |
| PVP (K-90) (%) | — | 0.2 |
| PVP (K-25) (%) | 0.2 | — |
| Sodium bicarbonate (%) | 0.014 | 0.01 |
| pH | 6.972 | 7.027 |
| log reduction (15 mins.) | 0.06 | 1.54 |

Examples 23-26

To demonstrate the effectiveness of low-chloride solutions with EDTA, PVP, and PHMB concentrations of 0.25 ppm with varying levels of phosphate buffer, several solutions according to the present invention were prepared by blending the following components:

| | |
|---|---|
| PHMB | 0.25 ppm |
| dexpanthenol | 0.02% |
| tyloxapol | 0.02% |
| Na$_2$HPO$_4$ | 0.01% |
| EDTA | 0.004% |
| PLURONIC F-68NF | 0.1% |
| PVP (K-90) | 0.2% |
| Sorbitol | 5% | and the following additional components as shown in Table 6. The solutions were tested against *C. albicans* with an inoculum level of 5.60 CFM/mL.

TABLE 6

| | Ex. 23 | Ex. 24 | Ex. 25 | Ex. 26 |
|---|---|---|---|---|
| Na$_2$HPO$_4$ (%) | 0.06 | 0.035 | 0.02 | 0.01 |
| pH | 7.036 | 6.996 | 7.013 | 7.000-7.146 |
| log reduction (15 mins.) | 1.81 | 1.37 | 2.56 | 2.71 |

Example 26

A solution according to the present invention was prepared by blending the following components:

| | |
|---|---|
| PHMB | 0.25 ppm |
| dexpanthenol | 0.2% |
| PLURONIC F-127 | 0.1% |
| Na$_2$HPO$_4$ | 0.001% |
| tyloxapol | 0.02% |
| sorbitol | 5% |

The pH was adjusted to neutral with phosphoric acid and/or sodium hydroxide and tonicity of the solution was within acceptable limits.

Example 27

A solution according to the present invention was prepared by blending the following components:

| | |
|---|---|
| PHMB | 0.25 ppm |
| dexpanthenol | 0.2% |
| PLURONIC F-127 | 0.1% |
| Na$_2$HPO$_4$ | 0.001% |
| tyloxapol | 0.02% |
| sorbitol | 5% |
| EDTA | 0.004% |

The pH was adjusted to neutral with phosphoric acid and/or sodium hydroxide and tonicity of the solution was within acceptable limits.

Example 28

A solution according to the present invention was prepared by blending the following components:

| | |
|---|---|
| PHMB | 0.25 ppm |
| dexpanthenol | 0.2% |
| PLURONIC F-127 | 0.1% |
| Na$_2$HPO$_4$ | 0.001% |
| tyloxapol | 0.02% |
| sorbitol | 2% |
| propylene glycol | 1% |

The pH was adjusted to neutral with phosphoric acid and/or sodium hydroxide and tonicity of the solution was within acceptable limits.

Example 29

A solution according to the present invention was prepared by blending the following components:

| | |
|---|---|
| PHMB | 0.25 ppm |
| dexpanthenol | 0.2% |
| PLURONIC F-127 | 0.1% |
| Na$_2$HPO$_4$ | 0.001% |
| tyloxapol | 0.02% |
| sorbitol | 5% |
| PVP (K-90) | 0.5% |

The pH was adjusted to neutral with phosphoric acid and/or sodium hydroxide and tonicity of the solution was within acceptable limits.

Example 30

A solution according to the present invention was prepared by blending the following components:

| | |
|---|---|
| PHMB | 0.25 ppm |
| dexpanthenol | 0.2% |
| PLURONIC F-127 | 0.1% |
| Na$_2$HPO$_4$ | 0.001% |
| tyloxapol | 0.02% |
| sorbitol | 5% |
| Pluronic 17R4 | 0.07% |

The pH was adjusted to neutral with phosphoric acid and/or sodium hydroxide and tonicity of the solution was within acceptable limits.

Example 31

A solution according to the present invention was prepared by blending the following components:

| | |
|---|---|
| PHMB | 0.25 ppm |
| dexpanthenol | 0.2% |
| Na$_2$HPO$_4$ | 0.001% |
| tyloxapol | 0.02% |
| sorbitol | 5% |
| PLURONIC acid F-68LF | 0.1% |

The pH was adjusted to neutral with phosphoric acid and/or sodium hydroxide and tonicity of the solution was within acceptable limits.

Example 32

A series of tests were conducted to evaluate the disinfecting performance against *C. albicans* of solutions prepared in accordance with Examples 26-31 compared with SoloCare PLUS solution.

TABLE 7

| Example | Polymeric Biguanide (ppm) | Log reduction (15 min.) |
|---|---|---|
| 26 | 0.25 | 0.6 |
| 27 | 0.25 | 2.6 |
| 28 | 0.25 | 3.1 |
| 29 | 0.25 | 2.1 |
| 30 | 0.25 | 2.2 |
| 31 | 0.25 | 1.8 |
| SOLOCARE | 1.0 | N/A* |

*There was no measurable difference in *C. Albicans* after 15 minutes of exposure to SoloCare in this experiment.

The present compositions provide a very beneficial and advantageous combination of performance efficacy and lens wearer/user comfort and acceptability. In the context of contact lens care solutions, lens wearer/user comfort and acceptability are very important, for example, to promote regular and effective treating of contact lenses. Such treating of contact lenses ultimately promotes ocular health and reduces the frequency of problems caused by wearing contact lenses. Thus, lens wearer/user comfort and acceptability are of substantial importance and benefit in a contact lens care product, in particular in the present compositions which exhibit substantial, even enhanced, lens wearer/user comfort and acceptability.

While this invention has been described with respect to various specific examples and embodiments, it is to be understood that the invention is not limited thereto and that it can be variously practiced within the scope of the following claims.

We claim:

1. An aqueous contact lens disinfecting solution, comprising:
   (a) less than 0.5 ppm PHMB;
   (b) 0.01% to 0.1% dexpanthenol;
   (c) 0.001% to 0.5% polyoxyethylene-polyoxypropylene block polymer;
   (d) 0.001% to 0.5% ethoxylated glucose derivative;
   (e) bis-TRIS-propane buffer;
   (f) 0.1% to 0.3% viscosity enhancing agent;
   (g) less than 0.2% chelating agent; and
   (h) at least 4% of a tonicity agent selected from the group consisting of glycerol, urea, propylene glycol, sodium bicarbonate, sugars, alcohols, polyols, and mixtures thereof; wherein said solution has a tonicity of 200 to 450 mOsm/kg, a pH of between 6 and 8, and a concentration of chloride ions below 500 ppm; and wherein said solution will result in at least a 1 log reduction in *C. albicans* within 15 minutes of contact.

2. An aqueous contact lens disinfecting solution as claimed in claim 1, wherein said chelating agent is EDTA; said viscosity enhancing agent is PVP; and said tonicity agent is sorbitol.

3. An aqueous contact lens disinfecting solution as claimed in claim 1, wherein said viscosity enhancing agent is PVP.

4. An aqueous contact lens disinfecting solution as claimed in claim 1, wherein said tonicity agent is sorbitol.

5. An aqueous contact lens disinfecting solution as claimed in claim 1, wherein said chelating agent is EDTA.

* * * * *